US011064976B2

(12) United States Patent
Tanigawa (10) Patent No.: US 11,064,976 B2
(45) Date of Patent: Jul. 20, 2021

(54) ULTRASONIC DIAGNOSTIC APPARATUS AND CONTROL PROGRAM THEREOF

(71) Applicant: General Electric Company, Schenectady, NY (US)

(72) Inventor: Shunichiro Tanigawa, Hino (JP)

(73) Assignee: General Electric Company, Schenectady, NY (US)

( * ) Notice: Subject to any disclaimer, the term of this patent is extended or adjusted under 35 U.S.C. 154(b) by 387 days.

(21) Appl. No.: 16/242,783

(22) Filed: Jan. 8, 2019

(65) Prior Publication Data

US 2019/0142384 A1    May 16, 2019

Related U.S. Application Data

(63) Continuation of application No. 14/422,752, filed as application No. PCT/US2013/055052 on Aug. 15, 2013, now abandoned.

(30) Foreign Application Priority Data

Aug. 21, 2012    (JP) ................................. 2012-182133

(51) Int. Cl.
*A61B 8/08* (2006.01)
*A61B 8/00* (2006.01)

(52) U.S. Cl.
CPC .............. *A61B 8/485* (2013.01); *A61B 8/085* (2013.01); *A61B 8/463* (2013.01); *A61B 8/5207* (2013.01); *A61B 8/5292* (2013.01); *A61B 8/5223* (2013.01)

(58) Field of Classification Search
CPC ...... A61B 8/485; A61B 8/5027; A61B 8/5292; A61B 8/085; A61B 8/463; A61B 8/5223
See application file for complete search history.

(56) References Cited

U.S. PATENT DOCUMENTS

2007/0112270 A1* 5/2007 Waki .................. A61B 8/14
600/455
2011/0306884 A1* 12/2011 Tanigawa ........... A61B 8/5223
600/443

* cited by examiner

*Primary Examiner* — Peter Luong (57) ABSTRACT

An ultrasonic diagnostic apparatus including an elastic image data generating unit which generates elastic image data having color information corresponding to strain calculated by a physical quantity data generating unit, and a displayer which causes an elastic image having a color corresponding to the strain to be displayed on an ultrasound image of the biological tissue, based on the elastic image data. The elastic image data generating unit generates the elastic image data, based on a color conversion table which is indicative of information of association of strain and the color information with each other and in which the color information changes depending on strain in a predetermined range of strain set in advance. The displayer displays an elasticity index image indicating an elasticity index indicative of a relative relationship of an average value of strain in a region set to the ultrasound image and the predetermined range of strain.

18 Claims, 6 Drawing Sheets

ULTRASONIC DIAGNOSTIC APPARATUS AND CONTROL PROGRAM THEREOF

CROSS-REFERENCE TO RELATED APPLICATIONS

The present application is a continuation of U.S. patent application Ser. No. 14/422,752, filed on Feb. 20, 2015, which is the National Stage of International Application No. PCT/US2013/055052, filed on Aug. 15, 2013, which claims priority from Japanese Patent Application No. 2012-182133, filed on Aug. 21, 2012, the entire contents of which are incorporated herein by reference.

BACKGROUND

Embodiments of the present invention relate to an ultrasonic diagnostic apparatus which displays an elastic image indicative of the hardness or softness of a biological tissue in a subject, and a control program thereof.

An ultrasonic diagnostic apparatus which combines a normal B-mode image and an elastic image indicative of the hardness or softness of a biological tissue in a subject together and displays the result of combination, has been disclosed in, for example, Japanese Patent Publication No. 2007-282932 or the like. The elastic image is generated in the following manner, for example. A physical quantity related to the elasticity of the subject is first calculated based on echo signals obtained by transmitting ultrasound to the subject. The physical quantity is strain, for example. An elastic image comprised of a color corresponding to the elasticity is generated based on the calculated physical quantity and displayed.

Meanwhile, there has recently been a demand for evaluation of a liver disease by an ultrasonic diagnostic apparatus capable of displaying an elastic image. Here, as for a diffuse liver disease, the elasticity of a liver may change in entirety without changing locally. Even in such a case, it has been desired that the elasticity of a biological tissue is recognized by the ultrasonic diagnostic apparatus to properly perform the evaluation of the disease.

BRIEF SUMMARY OF THE INVENTION

An embodiment of the invention made to solve the above problems is an ultrasonic diagnostic apparatus which is equipped with a physical quantity calculating unit which calculates a physical quantity related to elasticity of each part in a biological tissue, based on echo signals obtained by transmission/reception of ultrasound to and from the biological tissue, an elastic image data generating unit which generates elastic image data having information indicative of a display form corresponding to the physical quantity calculated by the physical quantity calculating unit, and a displayer which causes an elastic image having the display form corresponding to the physical quantity to be displayed on an ultrasound image of the biological tissue, based on the elastic image data. In the ultrasonic diagnostic apparatus, the elastic image data generating unit generates the elastic image data, based on information, the information being information in which the physical quantity and the information indicative of the display form are associated with each other, and in which the information indicative of the display form changes depending on a physical quantity in a prescribed range of physical quantities set in advance. The displayer displays an elasticity index image indicating an elasticity index indicative of a relative relationship between a typical value representative of a physical quantity in a region set to the ultrasound image and the prescribed range of physical quantities.

According to the above embodiment, since an elasticity index image indicating an elasticity index indicative of a relative relationship between a typical value representative of a physical quantity in a region set to the ultrasound image and the prescribed range of physical quantities is displayed, the elasticity of a biological tissue can be shown in a quantified form. It is thus possible to recognize the elasticity of the biological tissue and properly perform the evaluation of a disease.

DETAILED DESCRIPTION OF THE INVENTION

Embodiments of the present invention will hereinafter be described based on the accompanying drawings.

Figure 1:
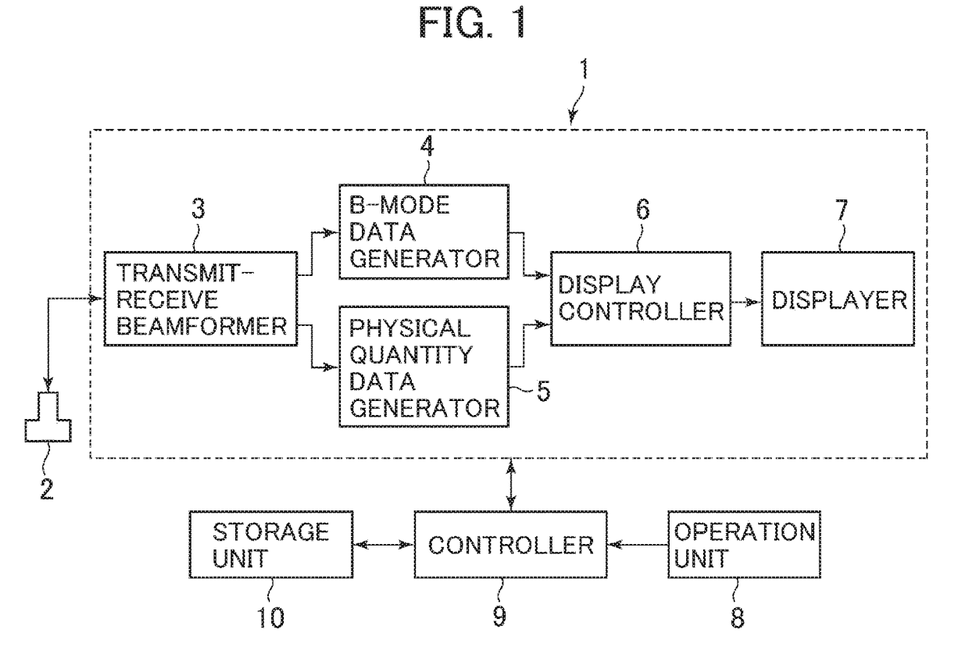
FIG. 1 is a block diagram showing one example of a schematic configuration of an embodiment of an ultrasonic diagnostic apparatus according to the present invention.

A first embodiment will first be explained based on FIGS. 1 through 8. An ultrasonic diagnostic apparatus 1 shown in FIG. 1 is equipped with an ultrasonic probe 2, a transmit-receive beamformer 3, a B-mode data generator 4, a physical quantity data generator 5, a display controller 6, a displayer 7, an operation unit 8, a controller 9 and a storage unit 10.

The ultrasonic probe 2 transmits ultrasound to a subject and receives its echoes. The transmit-receive beamformer 3 drives the ultrasonic probe 2 under a predetermined scan condition to perform the scanning of the ultrasound every sound ray. Also, the transmit-receive beamformer 3 performs signal processing such as phasing-adding processing on each echo received by the ultrasonic probe 2. Echo data subjected to the signal processing by the transmit-receive beamformer 3 is outputted to the B-mode data generator 4 and the physical quantity data generator 5. The transmit-receive beamformer 3 is one example illustrative of an embodiment of transmit-receive beamformer in the present invention.

The B-mode data generator 4 performs B-mode processing such as logarithmic compression processing, envelop detection processing or the like on the echo data outputted from the transmit-receive beamformer 3 to thereby generate B-mode data. The B-mode data may be stored in the storage unit 10.

The physical quantity data generator 5 calculates a physical quantity related to the elasticity of each portion in the subject, based on the echo data outputted from the transmit-receive beamformer 3 to generate physical quantity data (physical quantity calculating function). As described in, for example, Japanese Unexamined Patent Publication No. 2008-126079, the physical quantity data generator 5 sets correlation windows to echo data different in time on the same sound ray at one scanning surface. The physical quantity data generator 5 performs a correlation computation between the correlation windows to calculate a physical quantity related to the elasticity for each pixel, thereby generating physical quantity data corresponding to one frame. Accordingly, the physical quantity data corresponding to one frame is obtained from echo data corresponding to two frames, and an elastic image is generated as will be described later.

The physical quantity data generator 5 calculates strain as the physical quantity related to the elasticity in the present embodiment. That is, the physical quantity data is data about the strain. In the present embodiment, as will be described later, strain is calculated by the deformation of the liver due to the pulsation of the heart or blood vessels. The physical quantity data generator 5 is one example illustrative of an embodiment of a physical quantity calculating unit in the present invention. The physical quantity calculating function is one example illustrative of an embodiment of a physical quantity calculating function in the present invention.

The physical quantity data may be stored in the storage unit 10.

Figure 2:
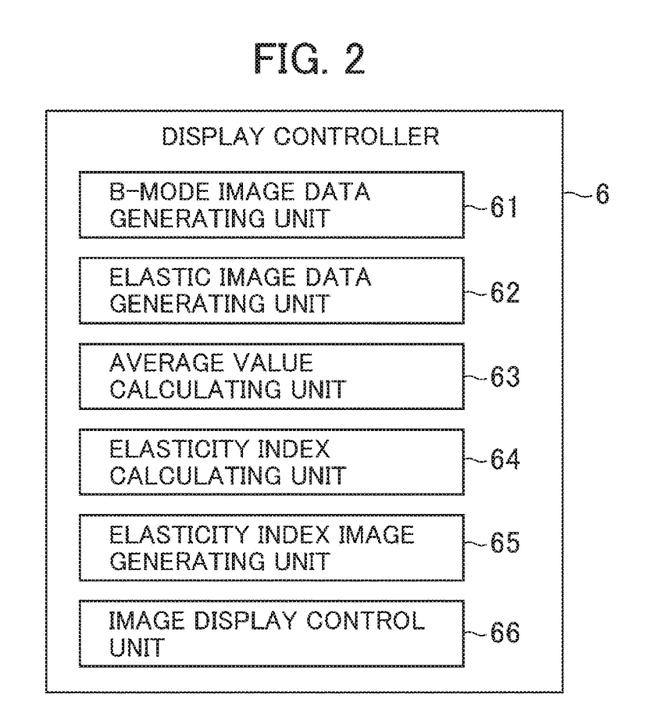
FIG. 2 is a block diagram illustrating a configuration of a display controller in the ultrasonic diagnostic apparatus shown in FIG. 1.

The display controller 6 is inputted with the B-mode data from the B-mode data generator 4 and the physical quantity data from the physical quantity data generator 5. As shown in FIG. 2, the display controller 6 has a B-mode image data generating unit 61, an elastic image data generating unit 62, an average value calculating unit 63, an elasticity index calculating unit 64, an elasticity index image generating unit 65, and an image display control unit 66.

The B-mode image data generating unit 61 performs scan conversion based on a scan converter on the B-mode data to convert it to B-mode image data having information indicative of brightness corresponding to the signal intensity of each echo. The B-mode image data has information indicative of brightness of 256 levels of gray, for example.

The elastic image data generating unit 62 converts the physical quantity data to information indicative of colors and performs scan conversion based on the scan converter to generate color elastic image data having information indicative of colors corresponding to strain (color elastic image data generating function). The elastic image data generating unit 62 brings physical quantity data into gradation and generates color elastic image data comprised of information indicative of colors assigned to respective gradations. The details thereof will be described later. The elastic image data generating unit 62 is one example illustrative of an embodiment of an elastic image data generating unit in the present invention. The color elastic image data is one example illustrative of an embodiment of elastic image data having information indicative of a display form corresponding to a physical quantity in the present invention. The information indicative of the display form is information indicative of each color in the present embodiment. The color elastic image data generating function is one example illustrative of an embodiment of an elastic image data generating function in the present invention.

The average value calculating unit 63 calculates an average value Stav of strain calculated by the physical quantity data generating unit 5 in a region R (refer to FIG. 3) set to a B-mode image BI as will be described later. This average value Stav of strain is one example illustrative of an embodiment of a value representative of a physical quantity of a region in the present invention. The average value calculating unit 63 is one example illustrative of an embodiment of a value calculating unit in the present invention.

The elasticity index calculating unit 64 calculates an elasticity index. The elasticity index is an index of the elasticity of a biological tissue in the region R. The elasticity index image generating unit 65 generates an elasticity index image indicative of the elasticity index calculated by the elasticity index calculating unit 64. The details thereof will be explained later. The elasticity index calculating unit 64 is one example illustrative of an embodiment of an elasticity index calculating unit in the present invention. The elasticity index image generating unit 65 is one example illustrative of an embodiment of an elasticity index image generating unit in the present invention.

The image display control unit 66 combines the B-mode image data and the color elastic image data together and generates image data of a composite ultrasound image displayed on the displayer 7. The image display control unit 66 causes the displayer 7 to display the image data as a composite ultrasound image UI obtained by combining a B-mode image BI and an elastic image EI (refer to FIG. 3). The elastic image EI is displayed in the region R set to the B-mode image BI.

The B-mode image data and the color elastic image data may be stored in the storage unit 10. The image data of the composite ultrasound image may be stored in the storage unit 10.

Figure 3:
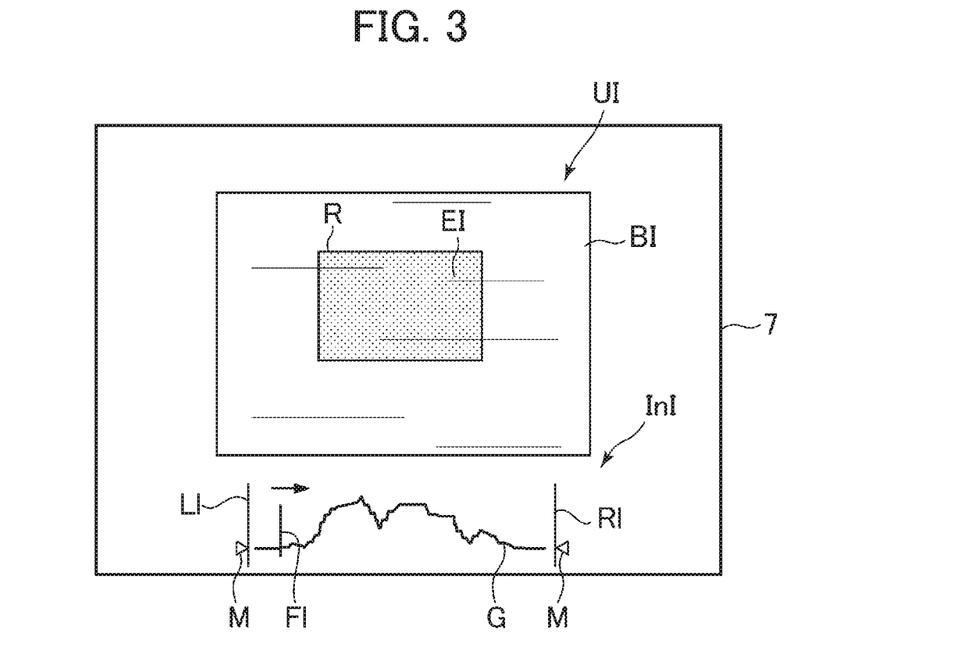
FIG. 3 is a diagram depicting one example of a composite ultrasound image displayed on a displayer.

The image display control unit 66 causes the displayer 7 to display an elasticity index image InI indicative of the elasticity index generated by the elasticity index image generating unit 65 along with the composite ultrasound image UI (refer to FIG. 3). The image display control unit 66 is one example illustrative of an embodiment of an image display control unit in the present invention and performs an image display control function in the present invention.

The displayer 7 is comprised of, for example, an LCD (Liquid Crystal Display), a CRT (Cathode Ray Tube) or the like. The displayer 7 is one example illustrative of an embodiment of a displayer in the present invention.

The operation unit 8 includes a keyboard and a pointing device (not shown) or the like for inputting instructions and information by an operator.

The controller 9 is comprised of a CPU (Central Processing Unit). The controller 9 reads a control program stored in the storage unit 10 to execute functions at the respective parts of the ultrasonic diagnostic apparatus 1, starting with the physical quantity calculating function, the color elastic image data generating function and the image display control function.

The storage unit 10 is, for example, an HDD (Hard Disk Drive), or a semiconductor memory such as a RAM (Random Access Memory), a ROM (Read Only Memory) or the like.

A description will now be made of the operation of the ultrasonic diagnostic apparatus 1 according to the present embodiment. The transmit-receive beamformer 3 causes the ultrasonic probe 2 to transmit ultrasound to a biological tissue of a subject. In the present embodiment, the ultrasound is transmitted to the liver of the subject by the ultrasonic probe 2.

The transmit-receive beamformer 3 may cause the ultrasonic probe 2 to alternately transmit ultrasound for generating a B-mode image and ultrasound for generating an elastic image. Echo signals of ultrasound transmitted from the ultrasonic probe 2 are received by the ultrasonic probe 2.

Here, the liver is repeatedly deformed depending on the pulsation of the heart or blood vessels. A composite ultrasound image that has taken deformation as strain is generated based on echo signals obtained from the liver in which such deformation has been repeated. Specifically, when the echo signals are captured, the B-mode data generator 4 generates B-mode data, and the physical quantity data generator 5 calculates strain to generate physical quantity data. Further, the B-mode image data generating unit 61 generates B-mode image data, based on the B-mode data, and the elastic image data generating unit 62 generates color elastic image data, based on the physical quantity data. Then, the image display control unit 66 causes the displayer 7 to display a composite ultrasound image UI in which a B-mode image BI based on the B-mode image data and an elastic image EI based on the color elastic image data are combined, as shown in FIG. 3. The composite ultrasound image UI is a real-time image. The elastic image EI is displayed within a region R (shown in dots).

The image display control unit 66 causes the displayer 7 to display the elasticity index image InI as shown in FIG. 3. The elasticity index image InI includes an elasticity index graph G indicative of changes in elasticity index with time. The details thereof will be described later.

A description will be made of the generation of the color elastic image data. The elastic image data generating unit 62 converts the physical quantity data to information indicative of colors (hereinafter called "color information"), based on a color conversion table TA to thereby generate the color elastic image data comprised of color information corresponding to a physical quantity. The color information is one example illustrative of an embodiment of information indicative of a display form in the present invention.

The color conversion table TA will be explained. The color conversion table TA is information in which strain and color information are associated with each other. Color information converted by this color conversion table TA is a prescribed number of gradations (0 to N). For example, the number of gradations is 256 (N=255).

Figure 4:
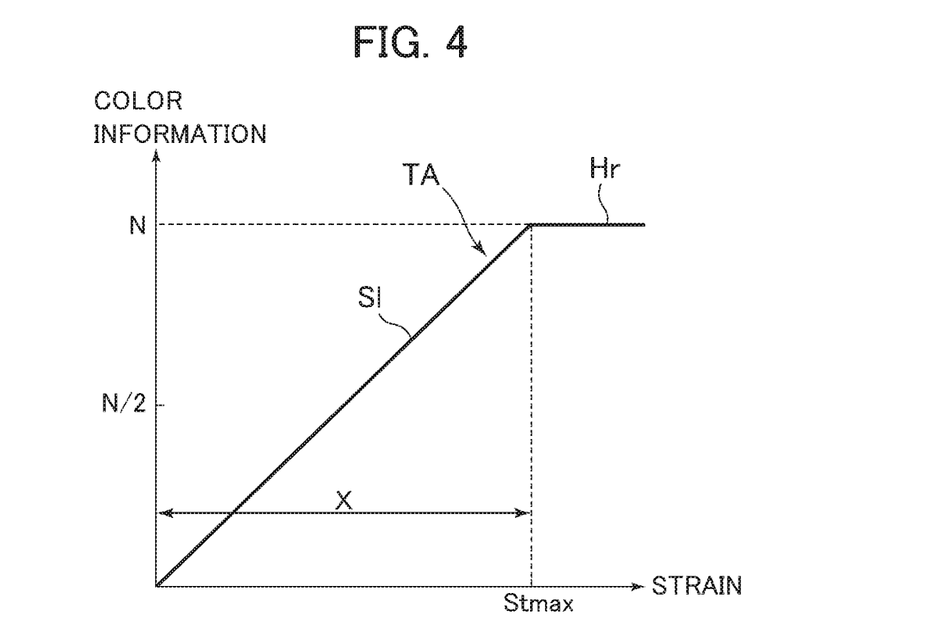
FIG. 4 is a diagram showing one example of a color conversion table.

The color conversion table TA can be shown in the graph shown in FIG. 4, for example. The color conversion table TA shown in FIG. 4 takes the form of a graph having a slope part S1 and a horizontal part Hr. In the present embodiment, a predetermined range X of strain extending from zero to strain Stmax corresponds to the slope part S1.

In the slope part S1, the color information is set so as to change stepwise depending on the strain. For example, the gradation 0 is color information indicative of blue, and the gradation N is color information indicative of red. The gradation N/2 being gradation in the middle between the gradation 0 and the gradation N is color information indicative of green. In this case, the color changes from blue to green between the gradation 0 and the gradation N/2, and the color changes from green to red between the gradation N/2 and the gradation N. The predetermined strain range X is one example illustrative of a predetermined range of physical quantities in the present invention.

The maximum value Stmax of strain in the predetermined strain range X is converted to the gradation N. Strain greater than or equal to the maximum value Stmax is converted to the gradation N. That is, strain is converted to the gradation N at the horizontal part Hr. Thus, the strain greater than or equal to the maximum value Stmax is represented in the same color (e.g., red) at an elastic image.

The predetermined strain range X is set in advance to a range of values of strain that the liver being targeted for the display of an elastic image can take according to the deformation of the liver due to the pulsation of the heart or blood vessels. For example, the predetermined strain range X is set to such a range that it includes from the value of strain of the normal liver to the value of strain of a liver of cirrhosis.

The elasticity index graph G will next be explained. The elasticity index graph G is a graph indicative of time changes in elasticity index In. The elasticity index In indicates a relative relationship between the average value Stav of strain in the region R and the predetermined range X of strain. This relative relationship means a position relationship of the average value Stav to the predetermined strain range X. Thus, the elasticity index In indicates in which position the average value Stav exists with respect to the predetermined strain range X.

The elasticity index In is calculated by the elasticity index calculating unit 64. Specifically, the elasticity index In is calculated by the following equation (1):

$$In = (\text{Average value Stav}/\text{Maximum value Stmax}) \times 100 \qquad (1)$$

Figure 5:
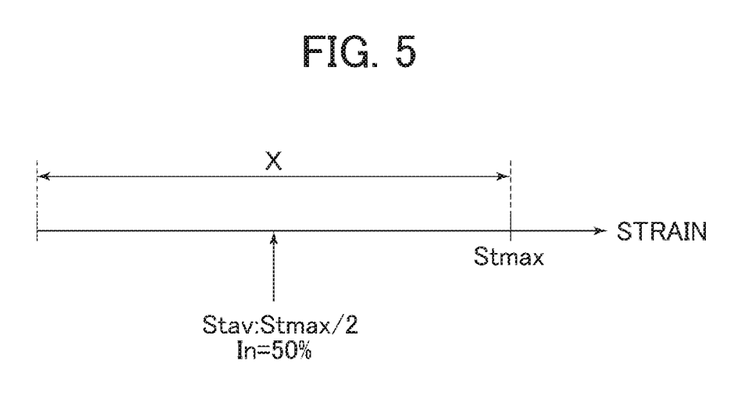
FIG. 5 is a diagram illustrating one example of an elasticity index in a strain range to which a slope part of the color conversion table is set.

The elasticity index In is a numeric value with a percent (%) as a unit. As shown in FIG. 5, for example, when the average value Stav of strain is of the central value of the strain range X, the elasticity index In is 50%. It is able to recognize from such an elasticity index In in which position the average value Stav of strain exists within the strain range X. It is able to grasp whether the elasticity of the region is hard or soft.

Incidentally, when the average value Stav of strain is larger than the maximum value Stmax (Stav>Stmax), the elasticity index In is taken as 100%.

Figure 6:
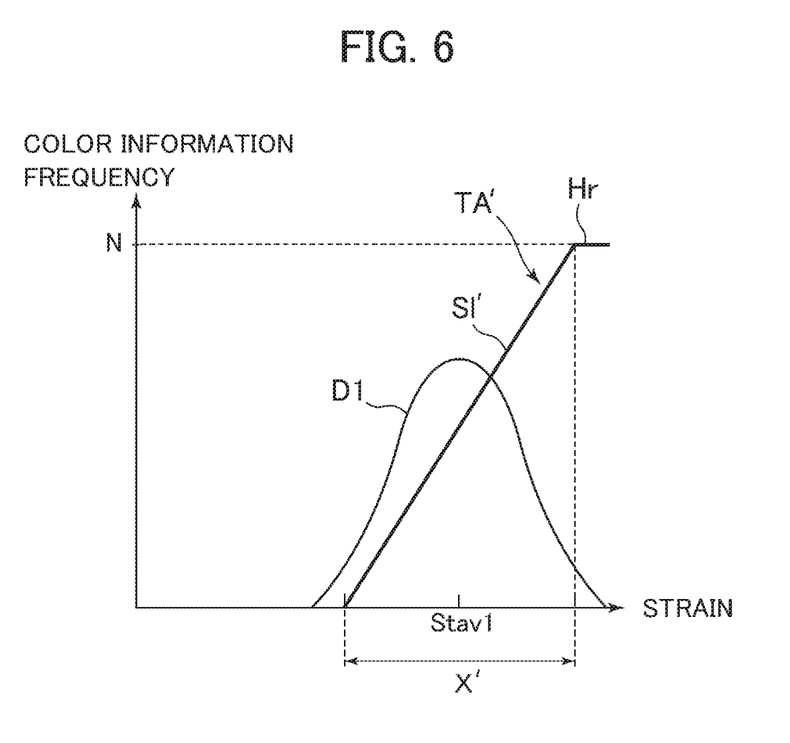
FIG. 6 is a diagram for describing a comparative example in which a color conversion table is set according to a distribution of strain.

Here, as an example compared with the present embodiment, a description will be made of a case where a color conversion table TA' is assumed to be set according to the distribution of strain in the region R to generate elastic image data. In FIG. 6, reference numeral D1 indicates the distribution of strain in the region R. The strain distribution D1 is a distribution of strain in the region R at a given frame.

Figure 7:
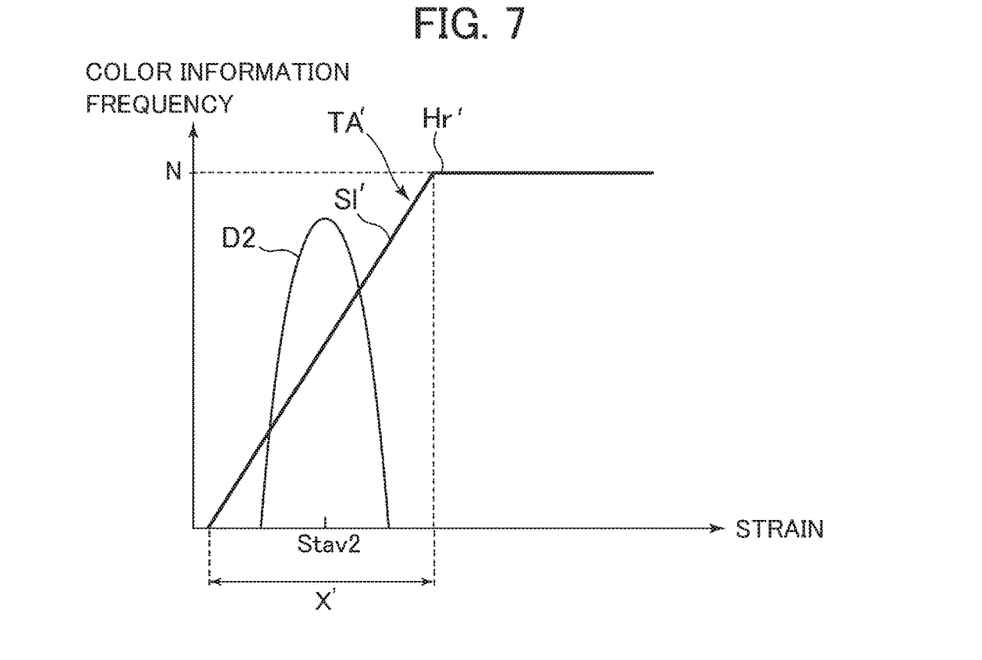
FIG. 7 is a diagram for describing a comparative example in which a color conversion table is set according to a distribution of strain.

In the color conversion table TA', a slope part S1' is set to a predetermined strain range X' on the basis of an average value Stav1 of strain in the strain distribution D1. Here, when the strain distribution D1 of FIG. 6 is taken as the normal liver, for example, the average value Stav1 is represented in green in an elastic image EI. On the other hand, assuming that a strain distribution D2 shown in FIG. 7 is a strain distribution about a liver hardened over its entirety, a slope part S1' is set to a predetermined strain range X' on the basis of an average value Stav2 of strain in the strain distribution D2. Even in the elastic image EI generated based on the color conversion table TA' to which such a slope part S1' is set, the average value Stav2 is represented in green in the elastic image EI. Thus, when the color conversion table TA' is set according to the distribution of strain, there is no difference in elastic image between the liver hardened over its entirety like cirrhosis and the normal liver.

Figure 8:
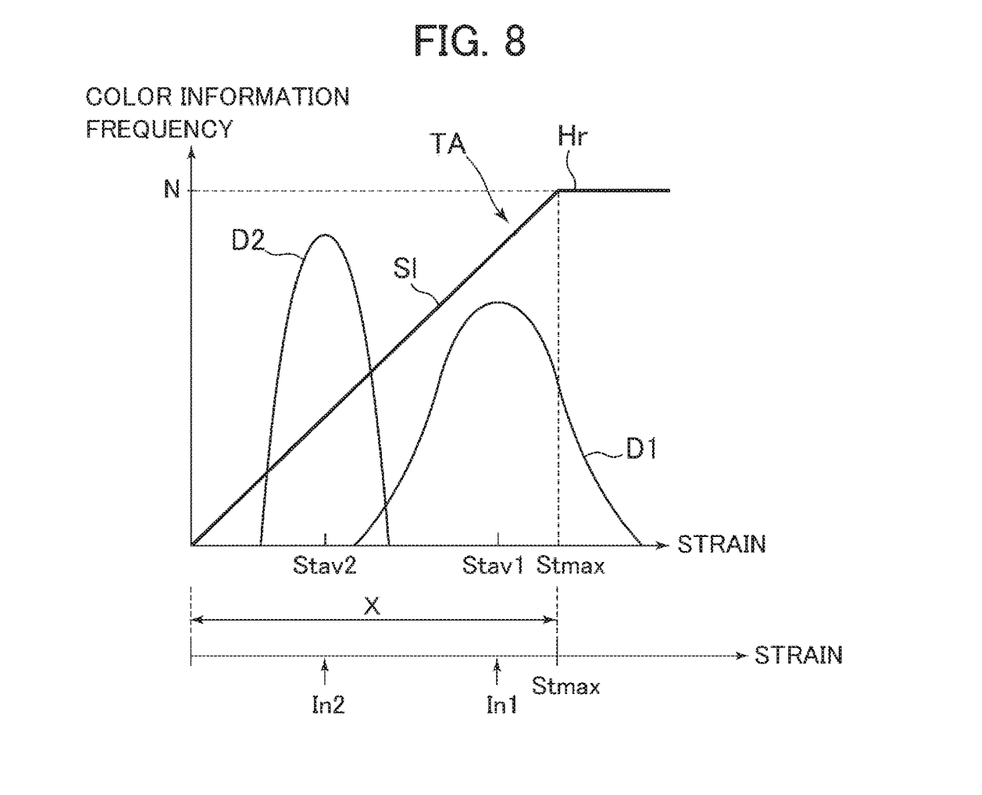
FIG. 8 is a diagram showing a color conversion table and elasticity indices in different strain distributions.

On the other hand, as in the present embodiment, the strain range to which the slope part S1 of the color conversion table TA is set, is fixed to a predetermined strain range X. The elastic index In indicative of the average value being located in any position is calculated in the range X. Therefore, the elastic index In becomes different values between the liver hardened over its entirety like cirrhosis and the normal liver. As shown in FIG. 8, for example, an elastic index In1 of an average value Stav1 of strain in the strain distribution D1 (the same strain distribution as in FIG. 6), and an elastic index In2 of an average value Stav2 of strain in the strain distribution D2 (the same strain distribution as in FIG. 7) become different values (In1>In2).

The elasticity index In is calculated for each frame of the elastic image EI. The elasticity index image generating unit 65 generates an elasticity index graph G indicative of time changes in the elasticity index In. The elasticity index graph G is displayed on the displayer 7 by the image display control unit 66.

The elasticity index image InI including the elasticity index graph G will be explained. The elasticity index image InI has a left line L1 (line), a right line R1, a zero point mark M, and an indication line F1 in addition to the elasticity index graph G. The elasticity index graph G is represented between the left line L1 and the right line R1. Between the left line L1 and the right line R1, the vertical direction indicates the size of an elasticity index In, and the horizontal direction indicates time. The zero point mark M means that the elasticity index In is 0%. The upper ends of the left line L1 and the right line R1 means that the elasticity index is 100%.

A point of intersection of the indication line F1 and the elasticity index graph G indicates an elasticity index In of an elastic image EI displayed on the displayer 7 at present. The indication line F1 moves in the right direction with the elapse of time. With the movement of the indication line F1, the elasticity index graph G is updated.

According to the present embodiment as described above, since the elasticity index graph G is displayed, the elasticity of a biological tissue can be shown in a quantified form. It is able to recognize by the elasticity index graph G, time changes in the strain of the biological tissue, repeated according to the heart rate or the pulsation of blood vessels, for example. It is thus possible to perform the evaluation of a disease in detail.

Figure 9:
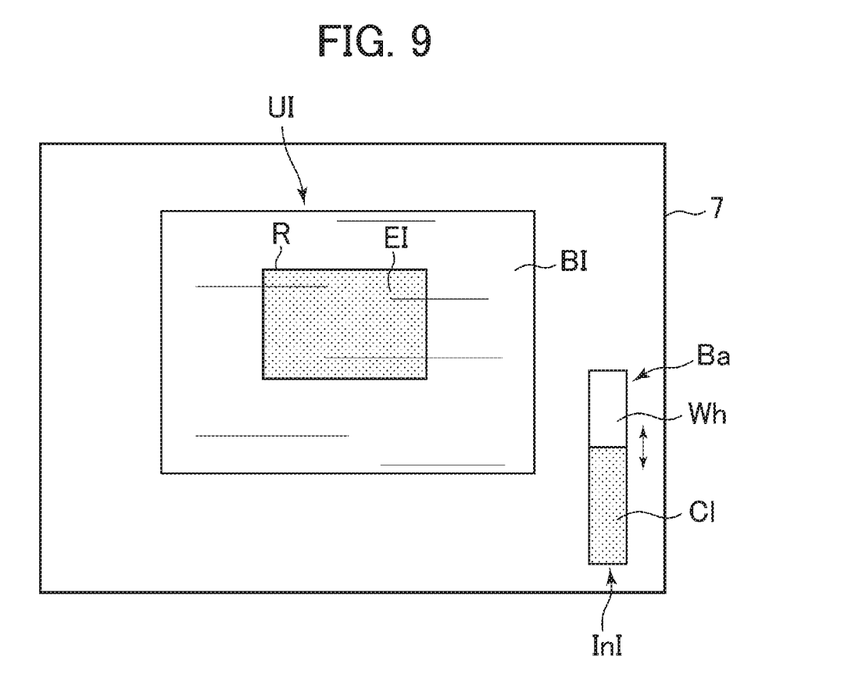
FIG. 9 is a diagram illustrating the displayer on which an elasticity index bar is displayed in a modification of the first embodiment.

A modification of the first embodiment will next be explained. In this modification, an elasticity index bar Ba is displayed as the elasticity index image InI as shown in FIG. 9. The elasticity index bar Ba is displayed at a part of which the background is black, and has a colored part Cl and a white part Wh. The length of the colored part Cl indicates the value of the elasticity index In. If the elasticity index In is 50%, for example, the colored part Cl becomes half of the overall length of the elasticity index bar Ba, and the white part Wh also becomes half of the overall length of the elasticity index bar Ba.

In the colored part Cl, the color thereof may be changed depending on the value of the elasticity index In. When the elasticity index In is greater than or equal to 0% and less than 30%, for example, the colored part Cl may be blue. When the elasticity index In is greater than or equal to 30% and less than 60%, the colored part Cl may be green. When the elasticity index In is greater than or equal to 60% and less than or equal to 100%, the colored part Cl may be red. The above numerical range and colors are however one example and not limited to the above.

As in this modification, the elasticity of a biological tissue can be shown in a quantified form even by the display of the elasticity index bar Ba.

A second embodiment will next be described. Description of the same items as those in the first embodiment is however omitted.

Figure 10:
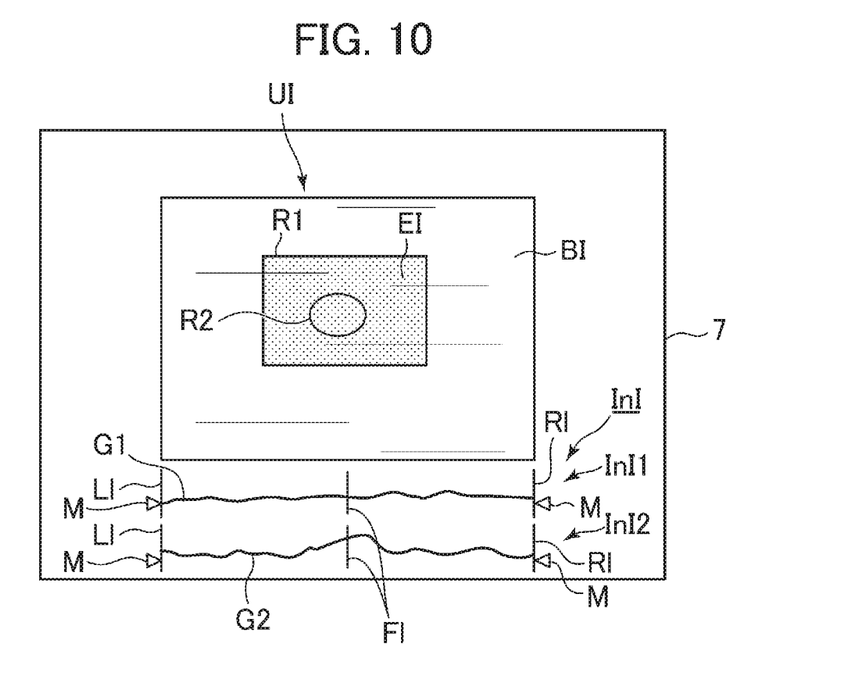
FIG. 10 is a diagram showing the displayer in a second embodiment.

In the present embodiment, as shown in FIG. 10, a first region R1 is set to a B-mode image BI displayed on the displayer 7. Further, a second region R2 is set to within the first region R1. The image EI is displayed in the first region R1 including the second region R2. For example, the second region R2 is set to a region that an operator takes interest in particularly within the first region R1.

In the present embodiment, the elasticity index calculating unit 64 calculates a first elasticity index In1 indicative of in which position an average value StavR1 of strain in the first region R1 exists within the predetermined strain range X, by the following (equation 2):

$$In1 = (\text{Average value } StavR1/\text{Maximum value } Stmax) \times 100 \quad (2)$$

Also the elasticity index calculating unit 64 calculates a second elasticity index In2 indicative of in which position an average value StavR2 of strain in the second region R2 exists within the predetermined strain range X, by the following (equation 3):

$$In2 = (\text{Average value } StavR2/\text{Maximum value } Stmax) \times 100 \quad (3)$$

The elasticity index image generating unit 65 generates a first elasticity index graph G1 indicative of time changes in the first elasticity index In1. Also the elasticity index image generating unit 65 generates a second elasticity index graph G2 indicative of time changes in the second elasticity index In2.

The image display control unit 66 causes the displayer 7 to display a first elasticity index image InI1 and a second elasticity index image InI2 as the elasticity index image InI as shown in FIG. 10. The first elasticity index image InI1 includes the first elasticity index graph G1 indicative of the time changes in the first elasticity index In1. The second elasticity index image InI2 includes the second elasticity index graph G2 indicative of the time changes in the second elasticity index In2. The first elasticity index image InI1 and the second elasticity index image InI2 are identical in configuration to the elasticity index image InI of the first embodiment, and their detailed description is therefore omitted.

According to the present embodiment described above, since the first elasticity index graph G1 and the second elasticity index graph G2 are displayed with respect to the first region R1 and the second region R2, the elasticity of the biological tissue in the two regions can be displayed in the quantified form. Time changes in the strain of the biological tissue in the two regions can be recognized by the first elasticity index graph G1 and the second elasticity index graph G2. It is thus possible to perform the evaluation of a disease in detail.

Figure 11:
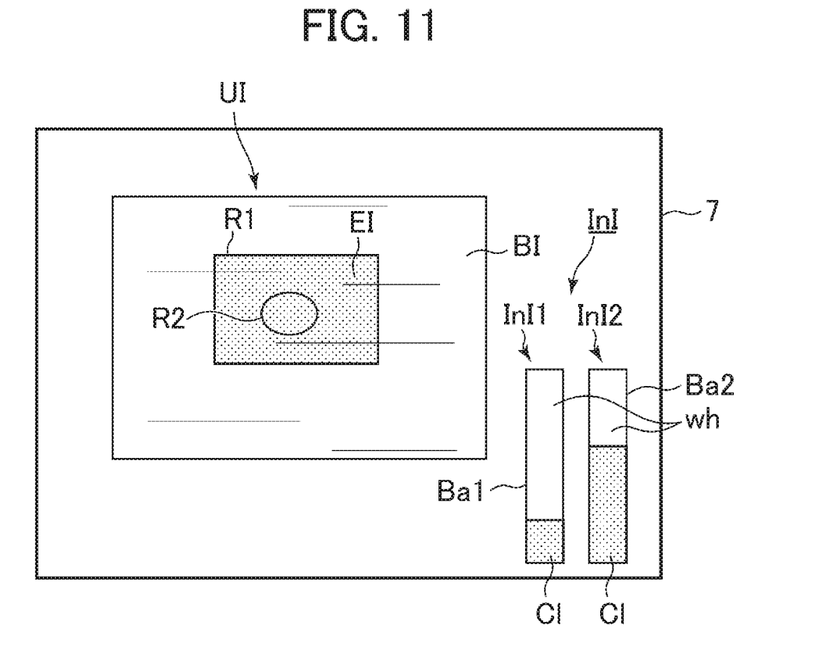
FIG. 11 is a diagram illustrating the displayer in a modification of the second embodiment.

A modification of the second embodiment will next be explained. In this modification, as with the modification of the first embodiment, as shown in FIG. 11, a first elasticity index bar Ba1 may be displayed as the first elasticity index image InI1, and a second elasticity index bar Ba2 may be displayed as the second elasticity index image InI2. The first elasticity index bar Ba1 is an image indicative of the value of the first elasticity index In1. The second elasticity index bar Ba2 is an image indicative of the value of the second elasticity index In2. The first elasticity index bar Ba1 and the second elasticity index bar Ba2 are identical in configuration to the elasticity index bar Ba in the modification of the first embodiment, and their detailed description is therefore omitted.

Although the present invention has been described above by the respective embodiments, it is needless to say that the present invention can be changed in various ways within the scope that does not change the gist of the invention. For example, although the elasticity index In is taken as 100% where the average value Stav of strain becomes larger than the maximum value Stmax in the above embodiment, the value obtained in each of the above equations (1), (2) and (3) may be defined as an elasticity index as it is. Accordingly, the value that exceeds 100% may be calculated as an elasticity index.

Figure 12:
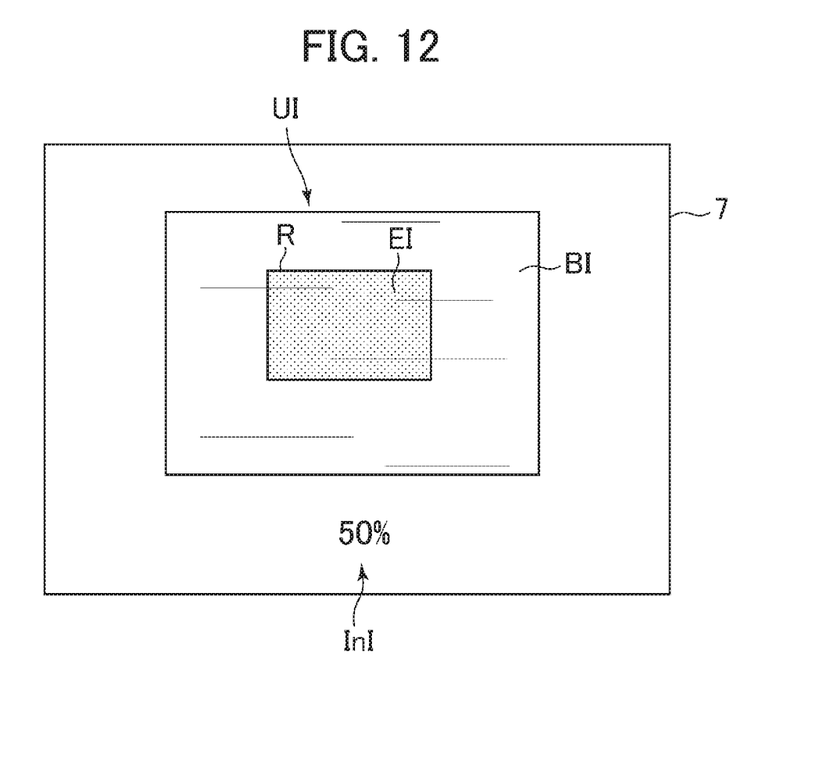
FIG. 12 is a diagram showing another example of an elasticity index image.

The elasticity index image InI may be a numeric value indicative of the value of an elasticity index In as shown in FIG. 12.

Further, in the second embodiment, the elasticity index image InI2 may be displayed only with respect to the region R2.

In the above equations (1) through (3), their common denominators are numeric values each indicative of the size of the range X of strain. When the minimum value of the strain range X is not zero, the difference between the maximum value of the strain range X and its minimum value becomes a common denominator.

The composite ultrasound image UI is not limited to the real-time image, but may be an image based on the data stored in the storage unit 10.

This written description uses examples to disclose the present invention, including the best mode, and also to enable any person skilled in the art to practice the present invention, including making and using any computing system or systems and performing any incorporated methods. The patentable scope of the present invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An ultrasonic diagnostic apparatus comprising:
a displayer; and
a processor, wherein the processor is configured to:
receive B-mode image data;
receive physical quantity data;
convert the physical quantity data to color elastic image data based on a color conversion table, where the color conversion table includes a predetermined physical strain quantity range including a first value of strain of a normal tissue to a second value of strain of a diseased tissue, where the physical strain quantity range does not vary based on a distribution of the physical quantity data;
combine the B-mode image data and the color elastic image data to generate a composite ultrasound image; and
cause the displayer to display the composite ultrasound image.

2. The ultrasonic diagnostic apparatus of claim 1, further comprising an ultrasonic probe configured to transmit ultrasound into a biological tissue and receive echo signals from the transmitted ultrasound, the biological tissue including a plurality of portions.

3. The ultrasonic diagnostic apparatus of claim 2, further comprising a B-mode data generator configured to perform B-mode processing on a first subset of the echo signals to generate B-mode data.

4. The ultrasonic diagnostic apparatus of claim 3, wherein the processor is further configured to perform scan conversion on the B-mode data to convert it to the B-mode image data.

5. The ultrasonic diagnostic apparatus of claim 4, further comprising a physical quantity data generator configured to calculate a strain related to the elasticity of the plurality of portions of the biological tissue based on a second subset of the echo signals to generate the physical quantity data.

6. The ultrasonic diagnostic apparatus of claim 5, wherein the normal tissue comprises a normal liver and the diseased tissue comprises a diseased liver.

7. The ultrasonic diagnostic apparatus of claim 6, wherein the diseased liver comprises a liver with cirrhosis.

8. The ultrasonic diagnostic apparatus of claim 1, wherein the normal tissue comprises a normal liver and the diseased tissue comprises a diseased liver.

9. The ultrasonic diagnostic apparatus of claim 8, wherein the diseased liver comprises a liver with cirrhosis.

10. The ultrasonic diagnostic apparatus of claim 1, wherein the processor is further configured to calculate an elasticity index of a specified region within the biological tissue.

11. The ultrasonic diagnostic apparatus of claim 10, wherein the processor is further configured to cause the displayer to display an elasticity index image indicative of the elasticity image.

12. The ultrasonic diagnostic apparatus of claim 11, wherein the displayer is configured to display the elasticity index image at the same time as the composite ultrasound image.

13. The ultrasonic diagnostic apparatus of claim 1, wherein the processor is further configured to calculate a value representative of a physical quantity within a specified region within a biological tissue.

14. The ultrasonic diagnostic apparatus of claim 13, wherein the processor is further configured to calculate an elasticity index of the specified region.

15. The ultrasonic diagnostic apparatus of claim 14, wherein the elasticity index indicates a position of the representative value in the predetermined physical strain quantity range.

16. The ultrasonic diagnostic apparatus of claim 15, wherein the processor is further configured to cause the displayer to display an elasticity index image indicative of the elasticity index at the same time as the composite ultrasound image.

17. The ultrasonic diagnostic apparatus of claim 16, wherein the value representative of the physical quantity within the specified region is an average value of the physical quantity within a region from which the physical quantity data is acquired.

18. The ultrasonic diagnostic apparatus of claim 1, wherein the color conversion table does not vary based on the distribution of the physical quantity data.

* * * * *